United States Patent
Park

(10) Patent No.: US 11,224,377 B2
(45) Date of Patent: Jan. 18, 2022

(54) METHOD OF MEASURING SKIN PIGMENTATION

(71) Applicant: INNSYS INC., Anyang-si (KR)

(72) Inventor: Chang Sik Park, Anyang-si (KR)

(73) Assignee: INNSYS INC.

(*) Notice: Subject to any disclaimer, the term of this patent is extended or adjusted under 35 U.S.C. 154(b) by 0 days.

(21) Appl. No.: 17/254,260

(22) PCT Filed: Apr. 5, 2019

(86) PCT No.: PCT/KR2019/004069
§ 371 (c)(1),
(2) Date: Dec. 18, 2020

(87) PCT Pub. No.: WO2019/245140
PCT Pub. Date: Dec. 26, 2019

(65) Prior Publication Data
US 2021/0259624 A1    Aug. 26, 2021

(30) Foreign Application Priority Data
Jun. 18, 2018  (KR) .................. 10-2018-0069551

(51) Int. Cl.
*A61B 5/00*       (2006.01)
*H04N 5/33*       (2006.01)

(52) U.S. Cl.
CPC .......... *A61B 5/443* (2013.01); *A61B 5/0082* (2013.01); *H04N 5/332* (2013.01)

(58) Field of Classification Search
CPC ....... A61B 5/0082; A61B 5/443; H04N 5/332
USPC .................. 348/77; 606/9; 600/306, 473
See application file for complete search history.

(56) References Cited

U.S. PATENT DOCUMENTS

| | | | | |
|---|---|---|---|---|
| 2004/0257439 | A1* | 12/2004 | Shirai | A61B 5/442 348/77 |
| 2008/0147053 | A1* | 6/2008 | Kang | A61B 5/441 606/9 |
| 2010/0130969 | A1* | 5/2010 | Batterson | A61B 18/203 606/9 |
| 2011/0304705 | A1* | 12/2011 | Kantor | A61B 5/0059 348/49 |
| 2015/0223749 | A1* | 8/2015 | Park | A61B 5/4875 600/473 |
| 2015/0313532 | A1* | 11/2015 | Marinkovich | G16H 50/20 600/306 |

(Continued)

*Primary Examiner* — Thai Q Tran
*Assistant Examiner* — Stephen R Smith
(74) *Attorney, Agent, or Firm* — Renaissance IP Law Group LLP

(57) ABSTRACT

A method of measuring skin pigmentation includes placing a camera at a target measurement position of skin, capturing an infrared image and an ultraviolet image of the skin by the camera, defining areas in the captured infrared image, generating digitized infrared pigmentation information by analyzing infrared pigment data in each of the area, defining areas in the captured ultraviolet image, generating digitized ultraviolet pigmentation information by analyzing ultraviolet pigment data in each of the areas, generating a pigmentation image by comparing the infrared pigmentation information with the ultraviolet pigmentation information in each of the same areas, and completing measurement by representing a numerical pigmentation degree of each area through analysis of the pigmentation image.

10 Claims, 5 Drawing Sheets

(56) References Cited

U.S. PATENT DOCUMENTS

| | | | |
|---|---|---|---|
| 2017/0150888 A1* | 6/2017 | Millikan | G01J 3/10 |
| 2020/0322521 A1* | 10/2020 | Houjou | A61B 5/0035 |
| 2020/0375466 A1* | 12/2020 | Ras | A61B 5/442 |

* cited by examiner

METHOD OF MEASURING SKIN PIGMENTATION

BACKGROUND

1. Field

The disclosure relates to a method of measuring skin pigmentation, and more particularly, to a method of measuring skin pigmentation, which increases the reliability and convenience of measurement by accurately measuring a pigmented position and a pigmentation degree through infrared and ultraviolet images that realize pigment properties of the skin as different pigment differences at a skin pigmentation measurement position.

2. Description of Related Art

In general, skin is a body organ that protects muscles and organs in the body, and plays a very important role in protecting the body from pathogens. Its other major functions include insulation, temperature regulation, sensation, synthesis of vitamin D, and the protection of vitamin B folates.

The skin is the largest organ in the human body and responds to internal and external stimuli of the skin by changing the pattern of pigmentation. Skin pigmentation is coloring different from normal skin. Although it is difficult to view pigmentation itself as a factor that determines health abnormalities, the pigmentation may be developed to skin diseases such as melanoma, basal cell carcinoma, and squamous cell carcinoma. Therefore, skin pigment detection plays a very important role not only cosmetically but also medically.

The main causes of variations in a skin color are melanin and hemoglobin components. The skin color turns pale yellow, reddish brown, or black depending on the level of melanin contained in the skin. Hemoglobin serves to supply oxygen to blood cells and thus causes the skin to appear red. Therefore, the degree and shape of skin pigmentation may be identified by analyzing the distribution of melanin and hemoglobin components in the skin. Visual examination is most widely used to determine skin pigmentation. Although this method is most often used by doctors and cosmetologists to determine pigmentation, test results are very subjective and not quantitative. Accordingly, there is a need for a quantitative method of determining the degree of skin pigmentation.

In this regard, a digital image analysis technique has recently been used to detect skin pigmentation, which may quantitatively measure the size and degree of a pigmented area as well as the pigmented area itself. A computer vision-based method of detecting skin pigmentation has been proposed. In this method, skin pigment asymmetry is set as a decision measure for skin lesions, and the degree of pigmentation is determined by detecting and quantifying the skin pigment asymmetry. Further, the fuzzy co-clustering algorithm for images (FCCI) technique has been extended to detect blotches of pigmented skin lesions, and a normalized entropy function is used to detect the features of blotches.

The existing pigmentation detection methods require stable illumination and high-performance dermoscopy during skin imaging in order to derive reliable and accurate results.

SUMMARY

Provided is a method of measuring skin pigmentation, which increases the reliability and convenience of measurement by accurately measuring a pigmented position and a pigmentation degree through infrared and ultraviolet images that realize pigmentation properties of the skin as different pigment differences at a skin pigmentation measurement position.

Additional aspects will be set forth in part in the description which follows and, in part, will be apparent from the description, or may be learned by practice of the presented embodiments of the disclosure.

According to an embodiment of the disclosure, a method of measuring skin pigmentation includes placing a camera at a target measurement position of skin, capturing an infrared image and an ultraviolet image of the skin by the camera, defining areas in the captured infrared image, generating digitized infrared pigmentation information by analyzing infrared pigment data in each of the area, defining areas in the captured ultraviolet image, generating digitized ultraviolet pigmentation information by analyzing ultraviolet pigment data in each of the areas, generating a pigmentation image by comparing the infrared pigmentation information with the ultraviolet pigmentation information in each of the same areas, and completing measurement by representing a numerical pigmentation degree of each area through analysis of the pigmentation image.

The capturing may include capturing the infrared image by controlling the camera positioned in an area to be captured by a photography controller, when an infrared light emitter emits infrared light under the control of a light emission controller, capturing the ultraviolet image by controlling the camera by the photography controller, when an ultraviolet light emitter emits ultraviolet light, and transmitting the infrared image and the ultraviolet image to an image transmitter.

The infrared pigmentation information may be obtained by dividing the received infrared image into a plurality of areas using xy coordinates by an area configure, and analyzing infrared pigment data being contrast values based on contrasts of a skin pigment and digitizing pigment differences by an infrared image analyzer.

The ultraviolet pigmentation information may be obtained by dividing the received ultraviolet image into a plurality of areas using xy coordinates by the area configure, and analyzing ultraviolet pigment data being contrast values based on contrasts of a skin pigment and digitizing pigment differences by an ultraviolet image analyzer.

The pigmentation image may be generated by comparing the infrared pigmentation information and the ultraviolet pigmentation information, which are generated with the pigment differences based on the contrast values, and selectively representing a pigmented area caused by contrast variations by a pigmentation image generator.

The completion may include calculating and representing measurement values according to pigmentation degrees of the pigmentation image generated based on contrast variations in the pigmentation image generator, by a pigmentation measurement data calculator.

The infrared pigmentation information may be a numerical representation obtained by dividing the received infrared image into a plurality of areas using xy coordinates by an area configurer, measuring red, green, blue (RGB) values of each of the areas, substituting wavelengths for the measured RGB values, and comparing wavelength values of light emitted from the infrared light emitter with observed wavelength values of the light reflected from the skin after reaction with the skin.

The ultraviolet pigmentation information may be a numerical representation obtained by dividing the received ultraviolet image into a plurality of areas using xy coordinates by the area configurer, measuring RGB values of each of the areas, substituting wavelengths for the measured RGB values, and comparing wavelength values of light emitted from the ultraviolet light emitter with observed wavelength values of the light reflected from the skin after reaction with the skin.

The pigmentation image may be generated by comparing the infrared pigmentation information and the ultraviolet pigmentation information, which are generated with the wavelength values substituting for the measured RGB values, and selectively representing a pigmented area caused by wavelength variations by a pigmentation image generator.

The completion may include calculating and representing measurement values according to pigmentation degrees of the pigmentation image generated according to wavelength variations in the pigmentation image generator, by a pigmentation measurement data calculator.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
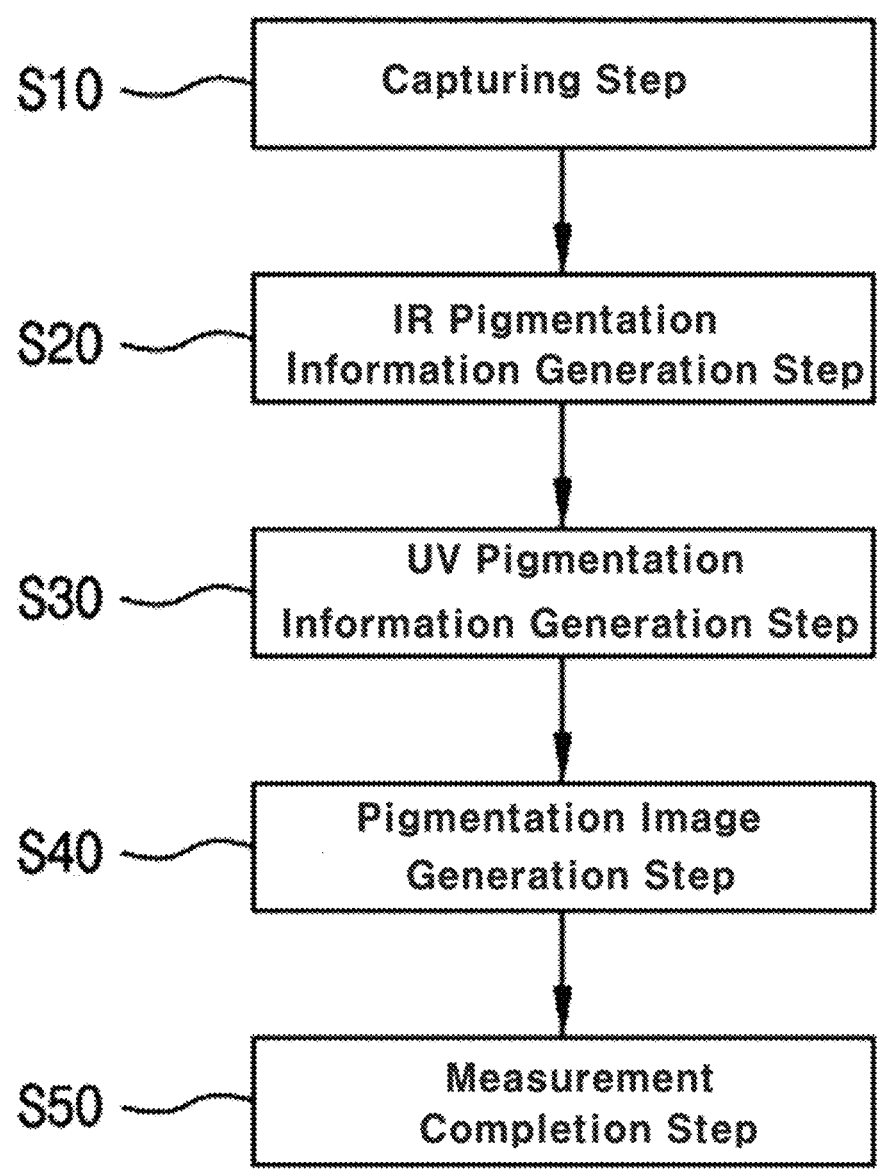
FIG. 1 is a flowchart illustrating a measurement step in a method of measuring skin pigmentation according to an embodiment of the disclosure.

It should be appreciated that various embodiments of the present disclosure and the terms used therein are not intended to limit the technological features set forth herein to particular embodiments and include various changes, equivalents, or replacements for a corresponding embodiment.

A detailed description of a known technology will be avoided in describing the disclosure, lest it should obscure the subject matter of the disclosure. As used herein, such terms as "1st" and "2nd," or "first" and "second" may be used to simply distinguish a corresponding component from another, and does not limit the components in other aspect.

It is to be understood that if an element is referred to, with or without the term "operatively" or "communicatively", as "coupled with," "coupled to," "connected with," or "connected to" another element, it means that the element may be coupled with the other element directly, wirelessly, or via a third element.

As used in connection with various embodiments of the disclosure, the terms "module" and "unit" in the following description are given or used interchangeably in consideration of only the ease of preparation of the specification, and do not have distinct meanings or roles. To clearly describe the disclosure, portions irrelevant to the description are omitted from the drawings. In the drawings, the widths, lengths, thicknesses, and so on of components may be exaggerated for convenience. Like reference numerals denote the same elements throughout the specification.

The disclosure will be described below in detail with reference to the attached drawings.

FIG. 1 is a flowchart illustrating a measurement step in a method of measuring skin pigmentation according to an embodiment of the disclosure.

Referring to FIG. 1, skin is captured at a measurement position, and its pigmentation state is measured through the captured image in the method of measuring skin pigmentation according to the embodiment of the disclosure.

The skin pigmentation measurement method includes capturing the skin (S10), generating infrared (IR) pigmentation information (S20), generating ultraviolet (UV) pigmentation information (S30), generating a pigmentation image (S40), and completing measurement (S50).

A measuring apparatus 100 used in the above-described method of measuring skin pigmentation includes a photographing unit 110 that captures the skin, and a measurement control unit 120.

In the capturing step S10, an IR image and a UV image are taken by placing a camera at a target measurement position of the skin and capturing the skin with the camera.

Figure 2:
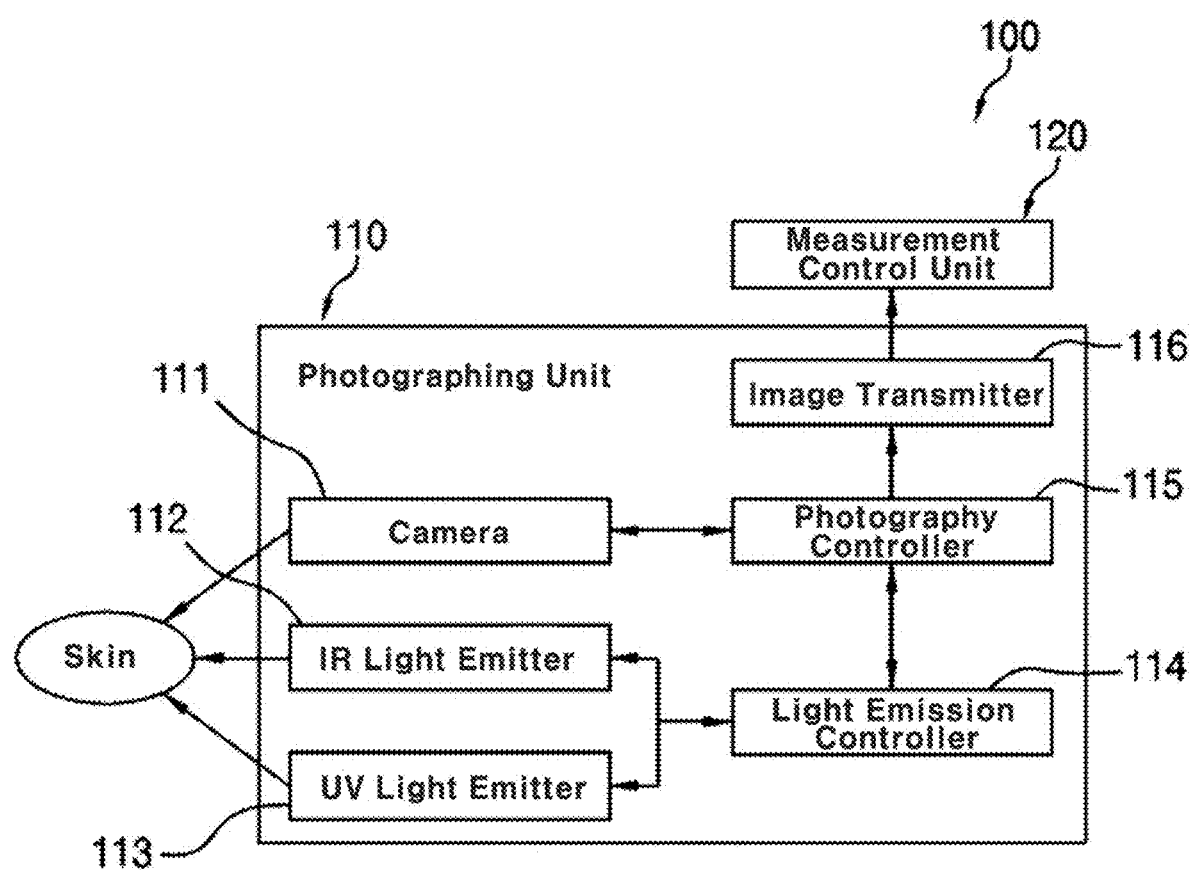
FIG. 2 is a block diagram illustrating a photographing unit which is a main component for implementing the method of measuring skin pigmentation illustrated in FIG. 1.

FIG. 2 is a block diagram illustrating the photographing unit which is a main component for implementing the method of measuring skin pigmentation illustrated in FIG. 1.

Referring to FIG. 2, the photographing unit 110 includes a camera 111 that captures the skin, an IR light emitter 112 that emits IR light, a UV light emitter 113 that emits UV light, a light emission controller 114 that controls emission of light from the IR light emitter 112 and the UV light emitter 113, a photography controller 115 that controls capturing of the camera 111, and an image transmitter 116 that transmits the IR image and the UV image captured by the camera 111 to the measurement control unit 120.

In the above-described capturing step S10 using the photographing unit 110, when the IR light emitter 112 emits IR light under the control of the light emission controller 114 while the camera 111 is positioned in an area to be captured, an IR image is captured by the camera 111 under the control of the photography controller 115. When the UV light emitter 113 emits UV light, a UV image is captured by the camera 111 under the control of the photography controller 115. The IR image and the UV image are then transmitted to the image transmitter 116. That is, an IR image is generated by capturing the skin with the camera 111 positioned over the target skin, while the IR light emitter 112 is emitting IR light under the control of the light emission controller 114, and then transmitted to the measurement control unit 120 through the image transmitter 116.

Further, a UV image is generated by capturing the skin with the camera 111 positioned over the target skin, while the UV light emitter 112 is emitting UV light under the control of the light emission controller 114, and then transmitted to the measurement control unit 120 through the image transmitter 116.

Figure 3:
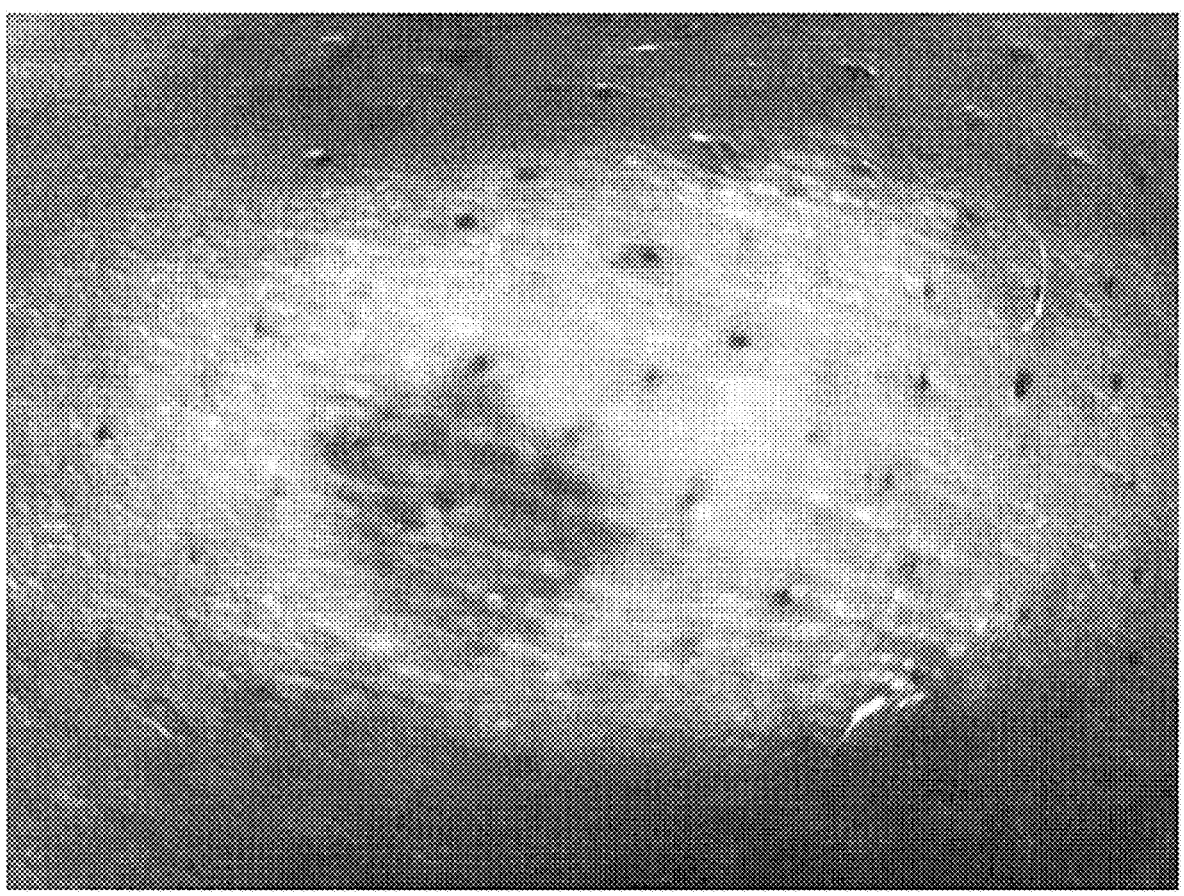
FIG. 3 is an infrared image captured by the photographing unit, with infrared light irradiated from an infrared light emitter in the method of measuring skin pigmentation illustrated in FIG. 1.

FIG. 3 is an IR image captured by the photographing unit while the IR light emitter is emitting IR light in the method of measuring skin pigmentation illustrated in FIG. 1.

As illustrated in FIG. 3, due to negative reaction to pigmentation, the IR image represents a skin state in which only hair roots, hair, and various blemishes appear in the form of pigments having contrast values, without contrast values of pigmentation.

Figure 4:
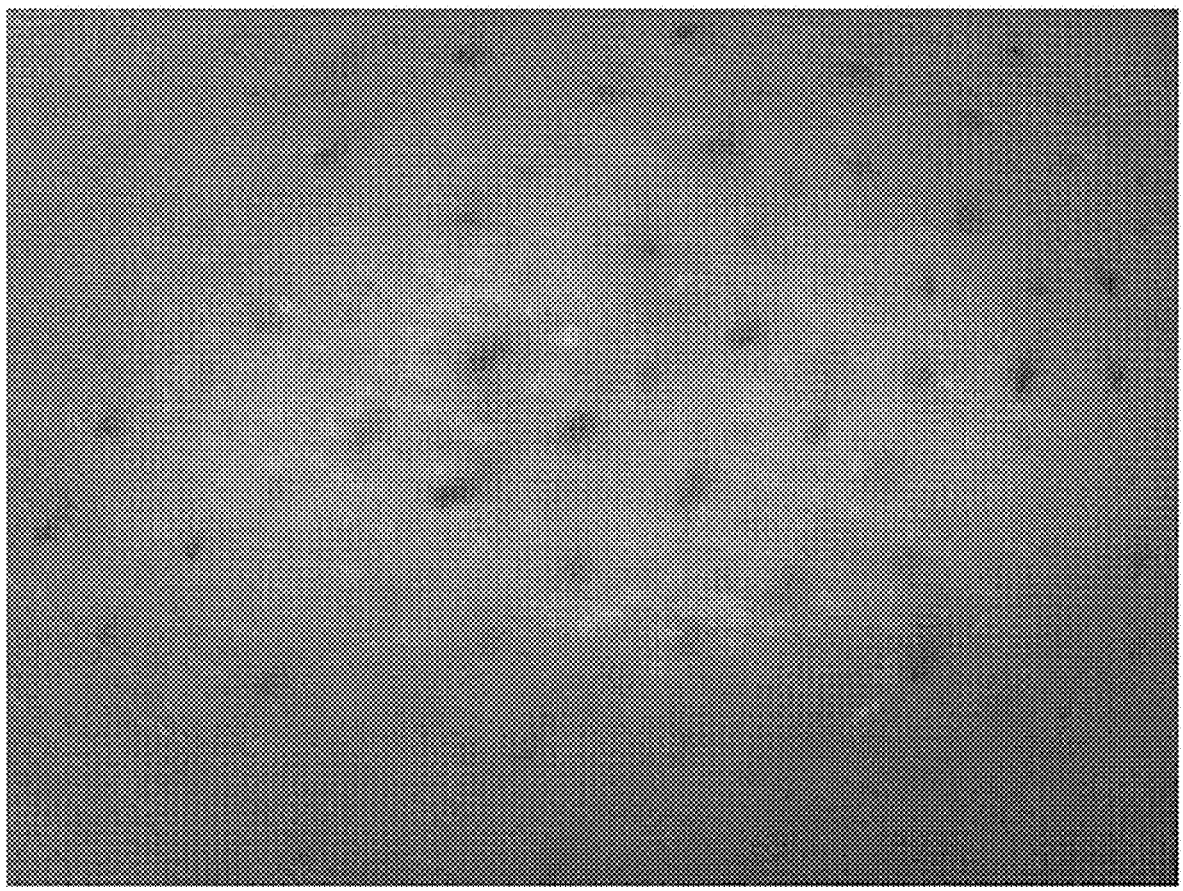
FIG. 4 is an ultraviolet image captured by the photographing unit, with ultraviolet light irradiated from an ultraviolet light emitter in the method of measuring skin pigmentation illustrated in FIG. 1.

FIG. 4 is a UV image captured by the photographing unit while the UV light emitter is emitting UV light in the method of measuring skin pigmentation illustrated in FIG. 1.

As illustrated in FIG. 4, due to positive reaction to pigmentation, the UV image represents a skin state in which hair roots, hair, and various blemishes appear in the form of pigments having contrast values, together with contrast values of pigmentation.

That is, use of pigment differences between the UV image with pigmentation and the IR image without pigmentation enables accurate detection of the degree and position of pigmentation.

Figure 5:
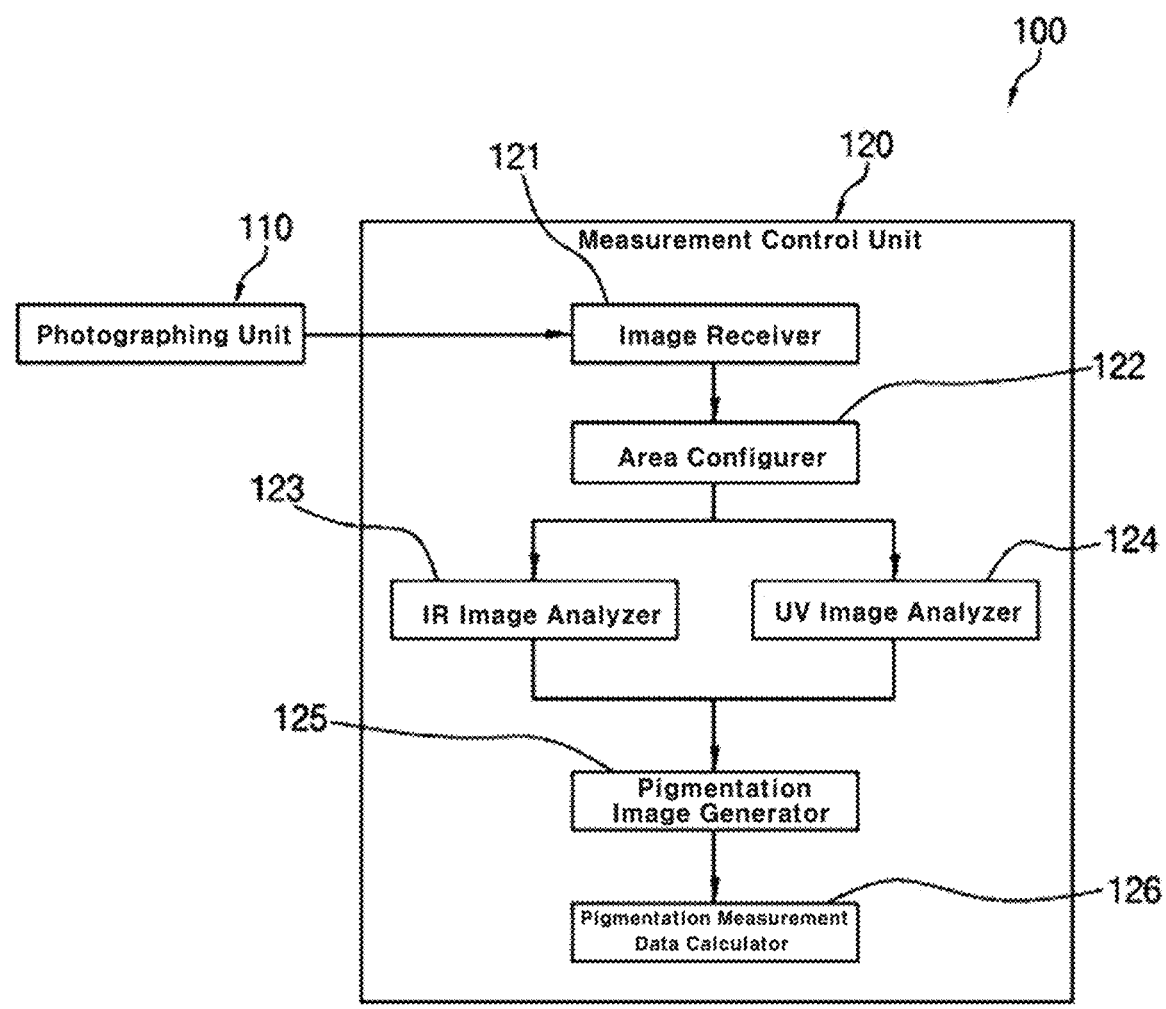
FIG. 5 is a block diagram illustrating an operational state of a measurement control unit which is a main component for implementing the method of measuring skin pigmentation illustrated in FIG. 1.

FIG. 5 is a block diagram illustrating an operational state of the measurement control unit, which is a main component for implementing the method of measuring skin pigmentation illustrated in FIG. 1.

Referring to FIG. 5, the measurement control unit 120 includes an image receiver 121 that receives an IR image and a UV image from the image transmitter 116 of the photographing unit 110, an area configurer 122 that divides each of the received images into a plurality of areas, an IR image analyzer 123 that analyses the received IR image, a UV image analyzer 124 that analyses the received UV image, a pigmentation image generator 125 that generates a pigmentation image according to pigmentation information analysed by the IR image analyzer 123 and the UV image analyzer 124, and a pigmentation measurement data calculator 126 that calculates a pigmentation value from the pigmentation image as data.

In the above-described IR pigmentation information generation step S20 using the measurement control unit 120, the captured IR image is divided into areas, and digitized IR pigmentation information is generated by analysing IR pigment data of each area.

The IR pigmentation information is a numerical representation of pigment differences, obtained by dividing the received IR image into a plurality of areas using xy coordinates by the area configurer 122, and analysing IR pigment data which is contrast values based on contrasts of the skin pigment in each of the areas by the IR image analyzer 123.

This IR pigmentation information provides information indicating whether elements having pigment values different from that of pigmentation, such as hair roots, hair, and blemishes of the skin exist in each area defined by the area configurer 122 in the IR image which negatively reacts to pigmentation and thus does not display the pigmentation. That is, the IR pigmentation information provides digitized contrast information for each area by determining brightness-based values with respect to a predetermined contrast value for the pigment, comparing a reference value with the areas defined by the area configurer 122, and thus digitizing brightness degrees which are contrasts by the IR image analyzer 123.

When contrast information is displayed on an area basis in the IR image, the positions and areas of hair roots, hair, and blemishes may be recognized from the IR pigmentation information.

In the above-described UV pigmentation information generation step S30, digitized UV pigmentation information is generated by defining areas in the captured UV image and analysing UV pigment data in each area.

The UV pigmentation information is a numerical representation of pigment differences, obtained by dividing the received UV image into a plurality of areas using xy coordinates by the area configurer 122, and analysing UV pigment data which is contrast values based on contrasts of the skin pigment in each of the areas by the UV image analyzer 124.

This UV pigmentation information provides information indicating whether elements having pigment values in a pigmented part exist along with hair roots, hair, and blemishes in the UV image which positively reacts to pigmentation and thus displays the pigmentation. That is, the UV pigmentation information provides digitized contrast information for each area by determining brightness-based values with respect to a predetermined contrast value for the pigment, comparing a reference value with the areas defined by the area configurer 122, and thus digitizing brightness degrees which are contrasts by the UV image analyzer 124.

When contrast information is displayed for each area in the UV image, the positions and areas of hair roots, hair, blemishes, and pigmented parts may be recognized from the UV pigmentation information.

In the pigmentation image generation step S40, a pigmentation image is generated by comparing the IR pigmentation information with the UV pigmentation information in each of the same areas.

The pigmentation image generator 125 generates the pigmentation image by selectively representing pigmented areas based on contrast variations, while comparing the IR pigmentation information and the UV pigmentation information which have been generated with pigment differences based on contrast values.

In other words, the pigmentation image generator 125 generates the pigmentation image displaying pigmented positions and the contrast values of brightnesses of the pigmented parts by comparing the UV pigmentation information including pigmentation data with the IR pigmentation information without pigmentation data.

In this manner, the pigmentation image represents the positions and brightness of pigmented parts without the hair roots, hair and blemishes within a skin measurement range. Specifically, as the hair roots, hair, and blemishes represented by the same pigment are removed by comparing the UV pigmentation information with the IR pigmentation information, the pigmentation image provides only information about the pigmented positions and brightness.

In the measurement completion step S50, the pigmentation degree of each area is represented as a numeral by analysing the pigmentation image, thus completing the measurement.

In the above-described measurement completion step S50, the pigmentation measurement data calculator 126 calculates and represents measurement values according to pigmentation degrees in the pigmentation image generated by the pigmentation image generator 125.

In this manner, the data values calculated by the pigmentation measurement data calculator 126 in the measurement completion step S50 is transmitted to a server and stored in the form of data. As the stored data may be transmitted to a remote location through a website to display the pigmentation image on a computer, the measured skin may be monitored through the pigmentation image even from a distance.

Since the measured skin may be monitored by long-distance transmission, a specialist may diagnose, treat, and manage the skin remotely.

A method of measuring skin pigmentation according to another embodiment of the present disclosure includes capturing the skin (S10), generating IR pigmentation information (S20), generating UV pigmentation information (S30), generating a pigmentation image (S40), and completing measurement (S50). The capturing step S10 is identical to a counterpart in the method of measuring skin pigmentation illustrated in FIGS. 1 to 5. Accordingly, the IR pigmentation information generation step S20, the UV pigmentation information generation step S30, the pigmentation image generation step S40, and the measurement completion step S50 will be described below.

According to another embodiment of the disclosure, the measurement control unit 120 includes the image receiver 121, the area configurer 122, the IR image analyzer 123, the UV image analyzer 124, the pigmentation image generator 125, and the pigmentation measurement data calculator 126.

The configuration illustrated in FIG. 5 is applied to the measurement control unit 120 because the measurement control unit 120 adopts only a different analysis scheme using wavelengths substituting for red, green, blue (RGB) values as an analysis tool, instead of contrasts.

In the IR pigmentation information generation step S20, digitized IR pigmentation information is generated by defining areas in a captured IR image and analysing IR pigment data in each area.

The IR pigmentation information is a numerical representation obtained by dividing the received IR image into a plurality of areas using xy coordinates by the area configurer 122, measuring RGB values in each of the areas, substituting wavelength values for the measured RGB values, and using the differences between wavelength values of light from the IR light emitter 112 and observed wavelength values of the light reflected from the skin after reaction with the skin by the IR image analyzer 123.

The infrared pigmentation information is a numerical representation of information indicating whether elements having pigment values other than pigmentation, such as hair roots, hair, and blemishes exist in each of the areas of the IR image in which pigmentation does not appear due to negative reaction to the pigmentation, obtained through wavelength substitution by the IR image analyzer 123.

In the process of generating IR pigmentation information in the IR image analyzer 123, RGB values are first measured in each of the areas of the received IR image.

The RGB values measured in the IR image are RGB values captured after IR light emitted from the IR light emitter 112 reacts with the skin and then is reflected from the skin. When the IR light is reflected from elements having pigment values other than pigmentation in each area, such as hair roots, hair, and blemishes of the skin, the RB values of the area are changed according to the chromaticity and intensity of the IR light.

When the measured RGB values are replaced with wavelengths, the wavelengths are different from each other in the areas of the hair roots, hair, and blemishes without pigmented parts. The wavelengths substituting for the RGB values measured in the above-described IR image are defined as observed wavelengths.

To replace an RGB value with a wavelength, the RGB value is converted to an hue, saturation, value (HSV) representation based on light intensity, the hue (H) (in degree) is converted to a frequency, and a wavelength is obtained using the frequency.

That is, the frequency is calculated by "frequency (THz) =474+(¾)Hue", and replaced with a wavelength calculated by "wavelength=the speed of light/frequency".

Particularly, the above-described IR image uses brightness-based contrast values without using various colours. Thus, the substitution may be facilitated by the above formula.

Numerical differences between wavelength values of light emitted from the IR light emitter 112 and observed wavelength values are used. Specifically, the differences are averaged and a numerical representation is obtained for each size based the average value.

The positions and concentrations of the hair roots, hair, and blemishes may be digitized into wavelengths based on the above-described numerals and represented in the image.

When wavelength information is displayed for each area of the IR image, the positions and areas of the hair roots, hair, and blemishes may be recognized from the IR pigmentation information.

The IR pigmentation information may also be represented as IR response indexes by replacing RGB values of a captured image of the skin irradiated with IR light with wavelengths.

In the UV pigmentation information generation step S30, digitized UV pigmentation information is generated by defining areas in a captured UV image and analysing UV pigment data in each area.

The UV pigmentation information is a numerical representation obtained by dividing the received UV image into a plurality of areas using xy coordinates by the area configurer 122, measuring RGB values in each of the areas, replacing the measured RGB values with wavelength values, and using the differences between wavelength values of light from the UV light emitter 113 and observed wavelength values of the light reflected from the skin after reaction with the skin by the UV image analyzer 124.

The UV pigmentation information is a numerical representation of information indicating whether elements having pigment values of pigmented parts exist along with hair roots, hair, and blemishes in each of the areas of the UV image in which pigmentation appears due to positive reaction to the pigmentation, obtained through wavelength substitution by the UV image analyzer 123.

In the process of generating UV pigmentation information in the UV image analyzer 124, RGB values are first measured in each of the areas of the received UV image.

The RGB values measured in the UV image are RGB values captured after UV light emitted from the UV light emitter 113 reacts with the skin and then is reflected from the skin. When the UV light is reflected from elements having pigment values hair roots, hair, blemishes, and pigmentation of the skin in each area, the RGB values of the area are changed according to the chromaticity and intensity of the UV light.

When the measured RGB values are replaced with wavelengths, the wavelengths are different from each other in the areas of the hair roots, hair, and blemishes without pigmented parts, and at pigmented positions. The wavelengths substituting for the RGB values measured in the above-described UV image are defined as observed wavelengths.

To replace an RGV value with a wavelength, the RGB value is converted to an HSV representation based on light intensity, the hue (H) (in degree) is converted to a frequency, and a wavelength is obtained using the frequency.

That is, the frequency is calculated by "frequency (THz) =474+(¾)Hue", and replaced with a wavelength calculated by "wavelength=the speed of light/frequency".

Particularly, the above-described UV image uses brightness-based contrast values without using various colours. Thus, the substitution may be facilitated by the above formula.

Numerical differences between wavelength values of light emitted from the UV light emitter 113 and observed wavelength values are used. Specifically, the differences are averaged and a numerical representation is obtained for each size based the average value.

The positions and concentrations of the hair roots, hair, blemishes, and pigmented areas may be converted into wavelengths based on the above-described numerals and represented in the image.

As wavelength information is displayed for each area of the UV image, the positions and areas of the hair roots, hair, blemishes, and pigmented parts may be recognized from the UV pigmentation information.

The UV pigmentation information may also be represented as UV response indexes by replacing RGB values of a captured image of the skin irradiated with UV light with wavelengths.

As described before, the IR pigmentation information is free of the wavelengths of pigmentation, whereas the UV pigmentation information includes the wavelengths of pigmentation. Therefore, a comparison between the IR pigmentation information and the UV pigmentation information enables measurement of the positions and degrees of pigmented parts on the skin.

In the pigmentation image generation step S40, a pigmentation image is generated by comparing the IR pigmentation information with the UV pigmentation information in each of the same areas.

The pigmentation image generator 125 generates the pigmentation image by selectively representing pigmented areas based on wavelength variations, while comparing the IR pigmentation information and the UV pigmentation information which have been generated with wavelength values by which measured RGB values are replaced.

In other words, the pigmentation image generator 125 generates the pigmentation image representing pigmented positions and the wavelength values of brightnesses of the pigmented parts by comparing the UV pigmentation information with pigmentation data with the IR pigmentation information without pigmentation data.

In this manner, the pigmentation image represents the positions and brightness of pigmented parts without the hair roots, hair and blemishes within a skin measurement range. Specifically, as the hair roots, hair, and blemishes represented by the same pigment are removed by comparing the UV pigmentation information with the IR pigmentation information, the pigmentation image provides only information about the pigmented positions and wavelengths.

In the measurement completion step S50, the pigmentation degree of each area is represented as a numeral by analysing the pigmentation image, thus completing the measurement.

In the above-described measurement completion step S50, the pigmentation measurement data calculator 126 calculates and represents measurement values according to pigmentation degrees in the pigmentation image generated by the pigmentation image generator 125.

In this manner, the data values calculated by the pigmentation measurement data calculator 126 in the measurement completion step S50 is transmitted to a server and stored in the form of data. As the stored data may be transmitted to a remote location through a website to display the pigmentation image on a computer, the measured skin may be monitored through the pigmentation image even from a distance.

In measuring the skin in the above-described pigmentation measurement method, not only pigmentation but also whether a cosmetic pigment remains after washing the face due to frequent use of cosmetics may be measured using pigment value differences resulting from irradiation of IR light and UV light.

Among pigment components used for mascara, carbon black is a main raw material of ink and provides the same pigment in IR light and UV light. Therefore, it is difficult to measure the carbon black by the above-described pigment difference-based measurement method.

Accordingly, since carbon black areas may be treated equally with hair roots, hair, and blemishes without pigment differences and thus removed, the carbon black areas may be measured based on measurement positions in consideration of shapes and patterns in a measured area.

As is apparent from the foregoing description, the method of measuring skin pigmentation according to the embodiments of the disclosure increases the reliability and convenience of measurement by accurately measuring a pigmented position and a pigmentation degree through IR and UV images that realize pigment properties of the skin as different pigment differences at a skin pigmentation measurement position.

Further, the method of measuring skin pigmentation according to the embodiments of the disclosure accurately detect a pigmented position by comparing an IR image in which a skin state such as hair roots and hair of the skin is represented as a pigment with a UV image in which a pigmented skin state as well as hair roots and hair of the skin is represented as a pigment. Therefore, the reliability of measurement increases.

Further, the apparatus for measuring a skin state by multiple light sources according to an embodiment of the disclosure represents the colors, size, and shape of a measurement target in an image by synthesizing images captured on a depth level basis from the surface of the skin using multiple lights. Therefore, the skin may be diagnosed by comparing the skin state with a disease sample, thereby increasing use convenience.

The above description is merely an illustrative description of the technical idea of the present disclosure. Those skilled in the art can make various variations and modifications without departing from the scope and spirit of the present disclosure.

Accordingly, the embodiments of the present disclosure are intended to describe the technical idea of the present disclosure, not limiting it.

The protection scope of the present disclosure should be defined by the appended claims, and all technical ideas within its equivalent scope should be interpreted as embraced in the scope of the present disclosure.

What is claimed is:

1. A method of measuring skin pigmentation, comprising:
    placing a camera at a target measurement position of skin, and capturing an infrared image and an ultraviolet image of the skin by the camera;
    defining areas in the captured infrared image, and generating digitized infrared pigmentation information by analyzing infrared pigment data in each of the areas;
    defining areas in the captured ultraviolet image, and generating digitized ultraviolet pigmentation information by analyzing ultraviolet pigment data in each of the areas;
    generating a pigmentation image by comparing the infrared pigmentation information with the ultraviolet pigmentation information in each of the same areas; and
    completing measurement by representing a numerical pigmentation degree of each area through analysis of the pigmentation image.

2. The method according to claim 1, wherein the capturing comprises:
- capturing the infrared image by controlling the camera positioned in an area to be captured by a photography controller, when an infrared light emitter emits infrared light under the control of a light emission controller;
- capturing the ultraviolet image by controlling the camera by the photography controller, when an ultraviolet light emitter emits ultraviolet light; and
- transmitting the infrared image and the ultraviolet image to an image transmitter.

3. The method according to claim 1, wherein the infrared pigmentation information is obtained by dividing the received infrared image into a plurality of areas using xy coordinates by an area configure, and analyzing infrared pigment data being contrast values based on contrasts of a skin pigment and digitizing pigment differences by an infrared image analyzer.

4. The method according to claim 3, wherein the ultraviolet pigmentation information is obtained by dividing the received ultraviolet image into a plurality of areas using xy coordinates by the area configure, and analyzing ultraviolet pigment data being contrast values based on contrasts of a skin pigment and digitizing pigment differences by an ultraviolet image analyzer.

5. The method according to claim 4, wherein the pigmentation image is generated by comparing the infrared pigmentation information and the ultraviolet pigmentation information, which are generated with the pigment differences based on the contrast values, and selectively representing a pigmented area caused by contrast variations by a pigmentation image generator.

6. The method according to claim 5, wherein the completion comprises calculating and representing measurement values according to pigmentation degrees of the pigmentation image generated based on contrast variations in the pigmentation image generator, by a pigmentation measurement data calculator.

7. The method according to claim 1, wherein the infrared pigmentation information is a numerical representation obtained by dividing the received infrared image into a plurality of areas using xy coordinates by an area configurer, measuring red, green, blue (RGB) values of each of the areas, substituting wavelengths for the measured RGB values, and using differences between wavelength values of light emitted from the infrared light emitter and observed wavelength values of the light reflected from the skin after reaction with the skin.

8. The method according to claim 7, wherein the ultraviolet pigmentation information is a numerical representation obtained by dividing the received ultraviolet image into a plurality of areas using xy coordinates by the area configurer, measuring RGB values of each of the areas, substituting wavelengths for the measured RGB values, and using differences between wavelength values of light emitted from the ultraviolet light emitter and observed wavelength values of the light reflected from the skin after reaction with the skin.

9. The method according to claim 8, wherein the pigmentation image is generated by comparing the infrared pigmentation information and the ultraviolet pigmentation information, which are generated with the wavelength values substituting for the measured RGB values, and selectively representing a pigmented area caused by wavelength variations by a pigmentation image generator.

10. The method according to claim 9, wherein the completion comprises calculating and representing measurement values according to pigmentation degrees of the pigmentation image generated according to wavelength variations in the pigmentation image generator, by a pigmentation measurement data calculator.

* * * * *